(12) United States Patent
Benkreira et al.

(10) Patent No.: US 10,510,065 B2
(45) Date of Patent: Dec. 17, 2019

(54) INTERACTING WITH AN AUTOMATED TELLER MACHINE USING A USER DEVICE

(71) Applicant: Capital One Services, LLC, McLean, VA (US)

(72) Inventors: Abdelkadar M'Hamed Benkreira, Washington, DC (US); Michael Mossoba, Arlington, VA (US); Joshua Edwards, Philadelphia, PA (US)

(73) Assignee: Capital One Services, LLC, McLean, VA (US)

( * ) Notice: Subject to any disclaimer, the term of this patent is extended or adjusted under 35 U.S.C. 154(b) by 0 days.

(21) Appl. No.: 15/974,610

(22) Filed: May 8, 2018

(65) Prior Publication Data
US 2019/0347641 A1    Nov. 14, 2019

(51) Int. Cl.
| | |
|---|---|
| *G06Q 20/32* | (2012.01) |
| *G06Q 20/10* | (2012.01) |
| *G07F 19/00* | (2006.01) |
| *G06Q 20/34* | (2012.01) |
| *H04M 1/725* | (2006.01) |
| *G06Q 20/40* | (2012.01) |

(52) U.S. Cl.
CPC ..... *G06Q 20/3223* (2013.01); *G06Q 20/1085* (2013.01); *G06Q 20/352* (2013.01); *G06Q 20/4012* (2013.01); *G07F 19/205* (2013.01); *H04M 1/7253* (2013.01)

(58) Field of Classification Search
CPC .......... G06Q 20/3223; G06Q 20/1085; G06Q 20/352; G06Q 20/4012; G07F 19/205; H04M 1/7253

USPC ........................................................ 705/7.21
See application file for complete search history.

(56) References Cited

U.S. PATENT DOCUMENTS

| | | | |
|---|---|---|---|
| 9,911,116 B1* | 3/2018 | Lewis | ........... G06Q 20/327 |
| 10,133,979 B1* | 11/2018 | Eidam | ........... G06K 19/0723 |
| 2005/0194446 A1* | 9/2005 | Wiklof | ........... G06K 7/0004 |
| | | | 235/462.46 |
| 2013/0238497 A1* | 9/2013 | Ramachandran | ...... G06Q 20/36 |
| | | | 705/41 |

(Continued)

OTHER PUBLICATIONS

EMV Issuer and Application Security Guidelines, EMVCo, LLC, Version 2.5, Oct. 2015, 82 pagees (Year: 2015).*

(Continued)

*Primary Examiner* — James D Nigh
(74) *Attorney, Agent, or Firm* — Harrity & Harrity, LLP

(57) ABSTRACT

A device may receive an indication that an ATM transaction is to be conducted, display prompt(s) for a user to input user authentication credential information and to select an ATM transaction type, detect user input(s) that include a user authentication credential and a selection of a particular ATM transaction type, and receive, from an ATM device, a request to establish a communication session. The ATM device may include a sync button to initiate communicative coupling of the ATM device and the user device. The request may be based on a user selection of the sync button. The device may communicatively couple to the ATM device, and provide, to the ATM device, the user authentication credential and data regarding the particular ATM transaction type to cause the ATM device to perform the ATM transaction. The device may display information regarding the ATM transaction.

20 Claims, 15 Drawing Sheets

(56) References Cited

U.S. PATENT DOCUMENTS

2019/0199714 A1* 6/2019 Kamal ............... H04L 63/0861

OTHER PUBLICATIONS

Brian Barrett, "Your Phone Will Replace Your Wallet at the ATM, Too" https://www.wired.com/2016/01/cardless-atms/, Jan. 28, 2016, 11 pages.
Bank of America, "Spend less time at the ATM, Use your phone to speed up your trip.", https://promo.bankofamerica.com/cardlessatm/, retrieved on Feb. 7, 2018, 3 pages.
Capital One, "Introducing CashTapp", https://www.capitalone.com/local/cashtapp-atm, Jan. 28, 2018, 4 pages.
Jon Fingas, "Tap your phone to withdraw cash from Wells Fargo ATMs", https://www.engadget.com/2017/10/10/wells-fargo-atms-offer-nfc-cash-withdrawals/, Oct. 10, 2017, 5 pages.
Alex Perala, "New ATM Uses Smartphone Interface, Facial Recognition for Withdrawals", https://mobileidworld.com/atm-smartphone-facial-recognition-withdrawls-006123/, Jun. 12, 2017, 4 pages.
"Contactless Specifications for Payment Systems," EMV Book B—Entry Point Specification, (Jul. 2016), downloaded from https://www.emvco.com/wp-content/uploads/2017/05/BookB_Entry_Point_Specification_v2_6_20160809023257319.pdf, 52 pages.

* cited by examiner

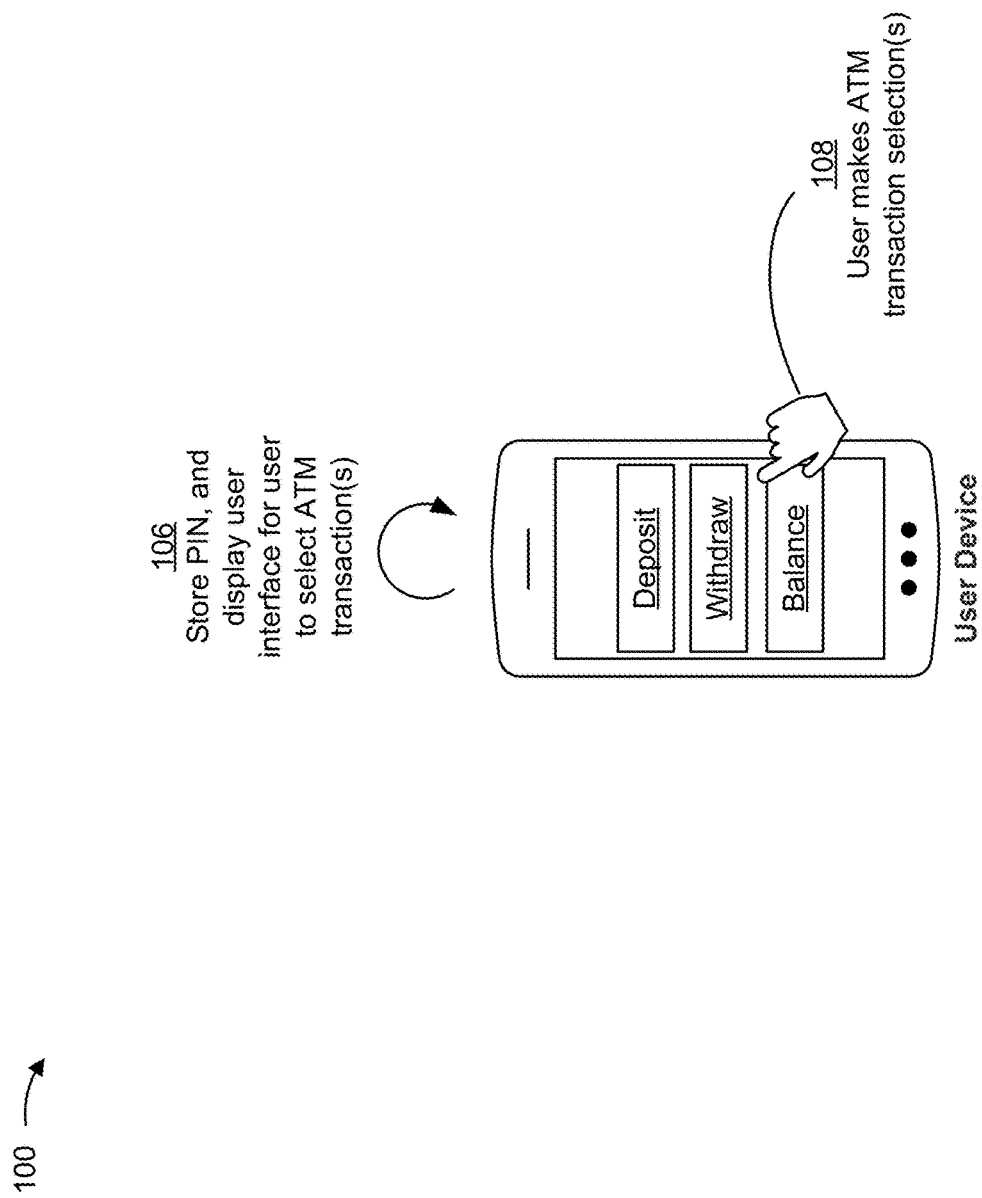

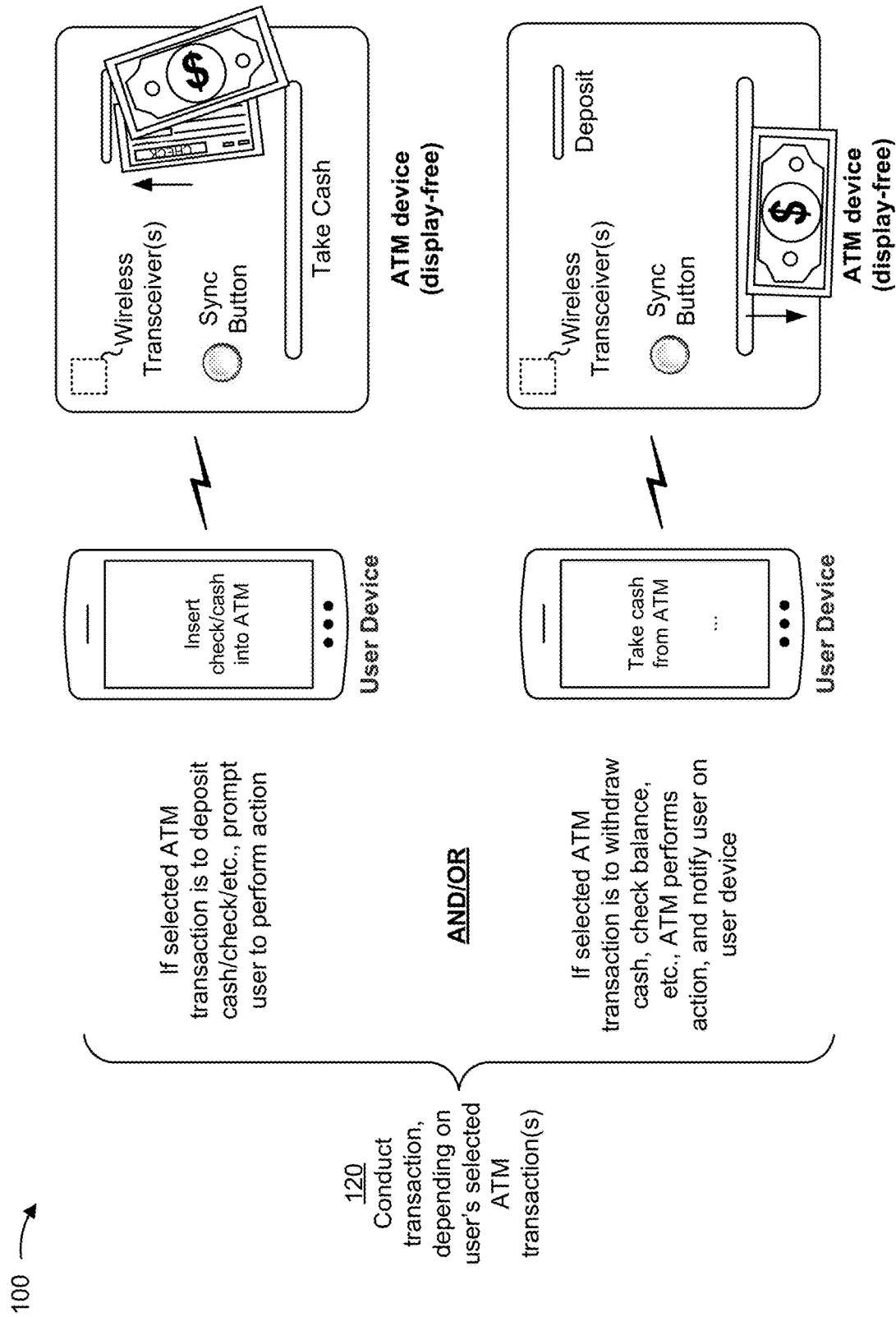

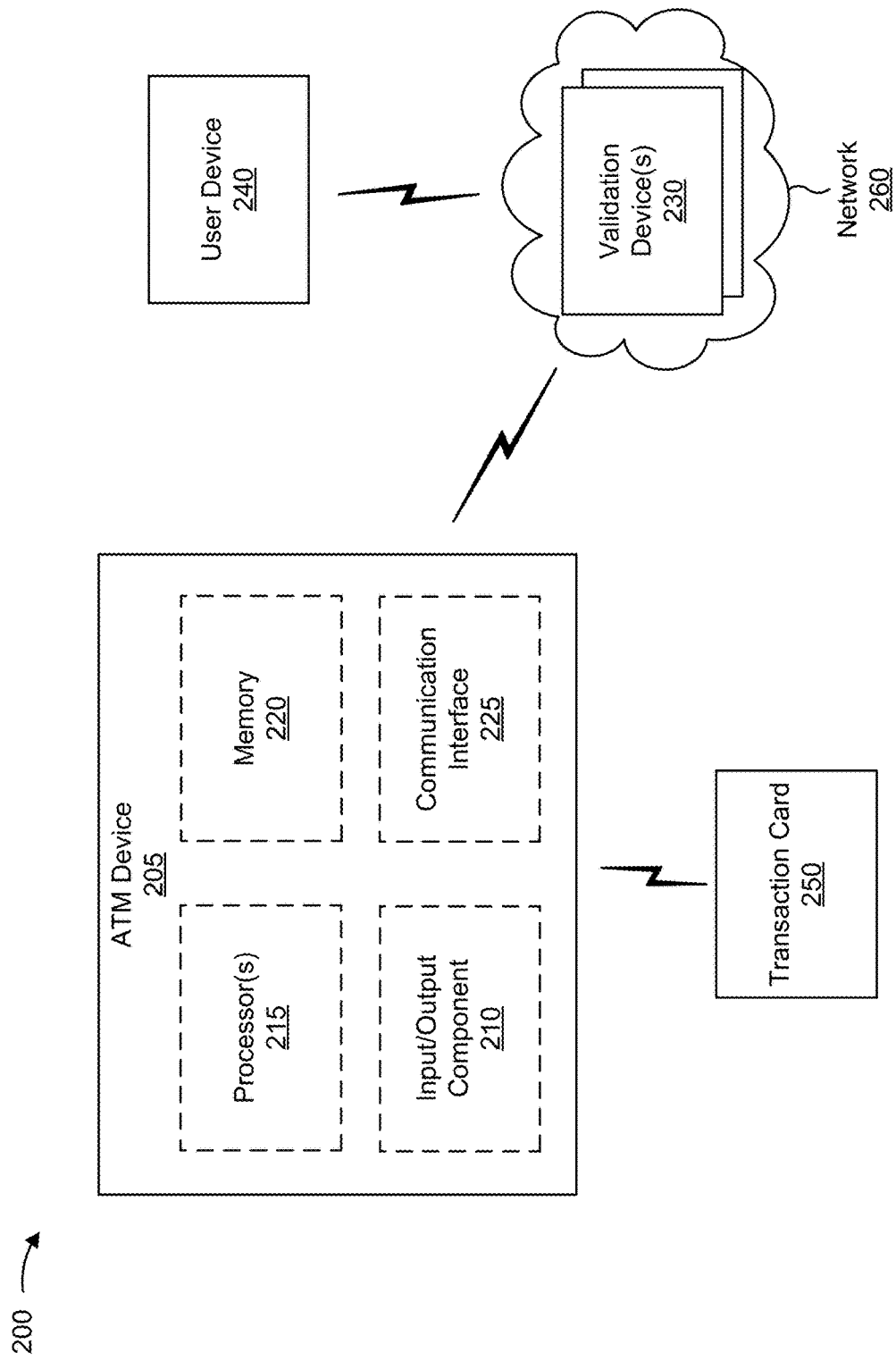

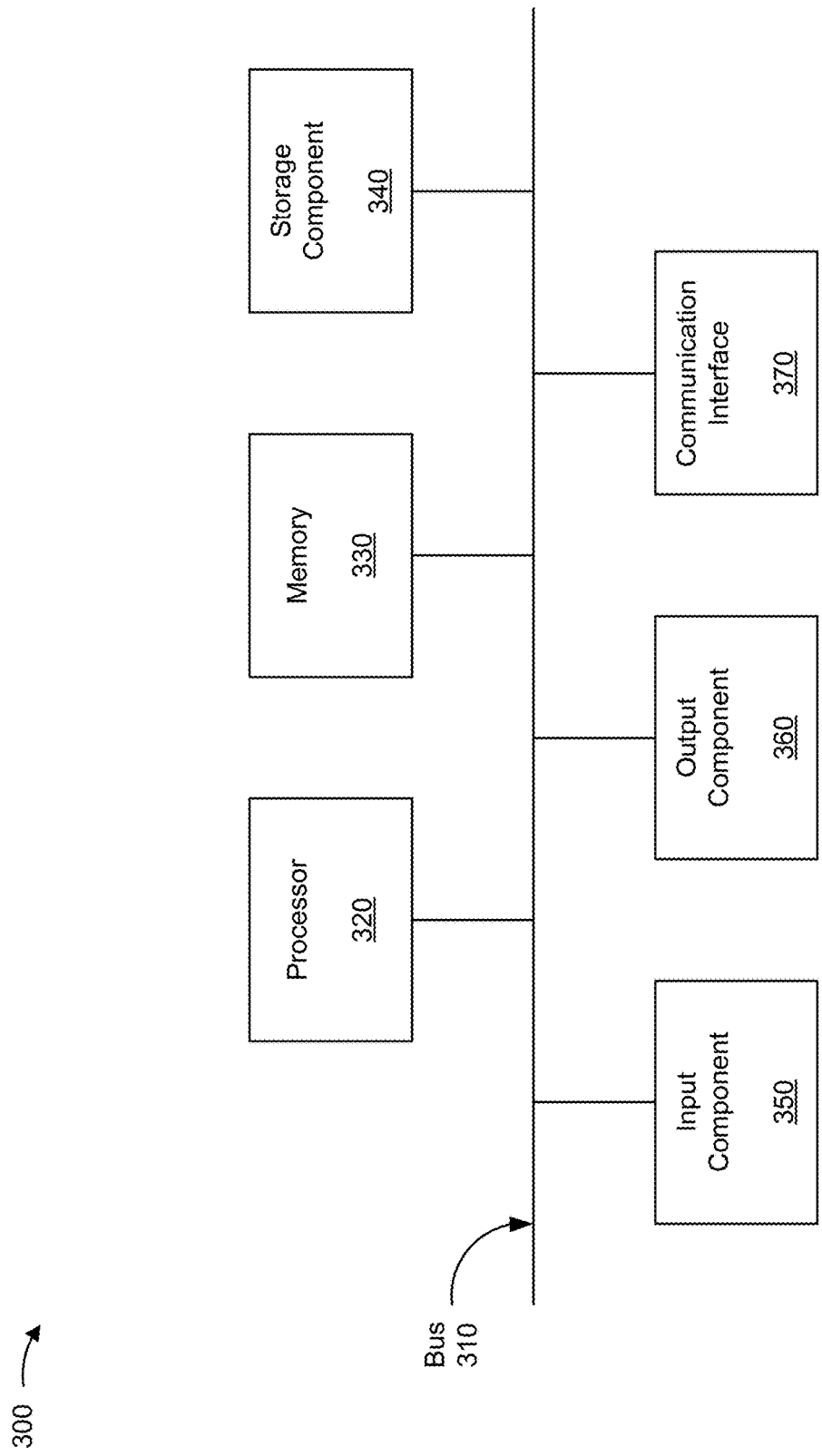

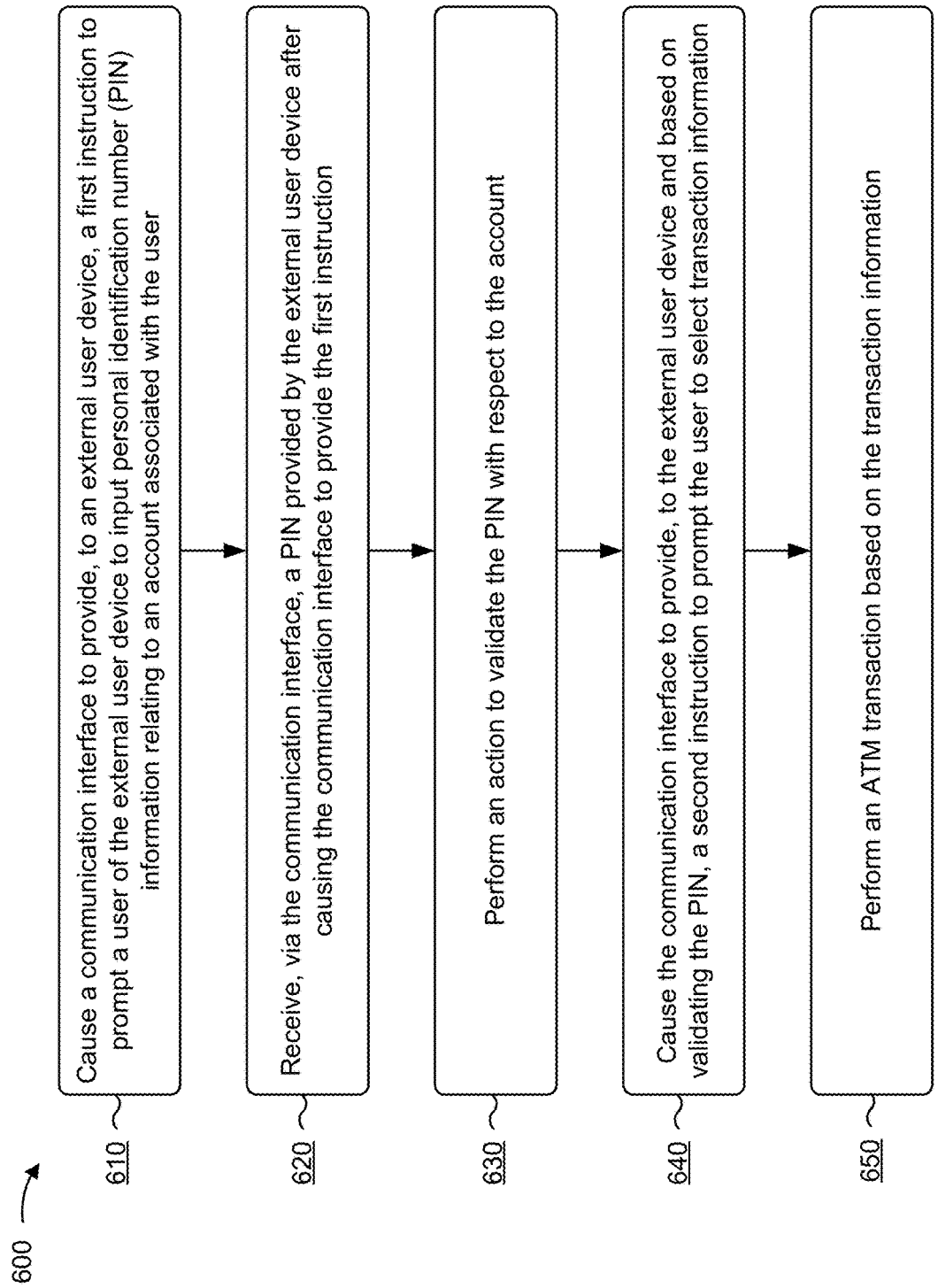

INTERACTING WITH AN AUTOMATED TELLER MACHINE USING A USER DEVICE

BACKGROUND

An automated teller machine (ATM) is an electronic device that permits users to perform various financial transactions, such as withdrawing and depositing cash, obtaining account-related information, and/or the like.

SUMMARY

According to some possible implementations, a method may include receiving, by a user device, an indication that an ATM transaction is to be conducted; displaying, by the user device, one or more prompts, for a user to input user authentication credential information, and to select an ATM transaction type, based on receiving the indication; detecting, by the user device, one or more user inputs that include a user authentication credential and a selection of a particular ATM transaction type after displaying the one or more prompts; receiving, by the user device and from an ATM device, a request to establish a communication session after detecting the one or more user inputs, the ATM device including a sync button to initiate communicative coupling of the ATM device and the user device, the request being based on a user selection of the sync button; communicatively coupling, by the user device, to the ATM device based on receiving the request; providing, by the user device, to the ATM device, and based on communicatively coupling to the ATM device, the user authentication credential and data regarding the particular ATM transaction type to cause the ATM device to perform the ATM transaction; and displaying, by the user device, information regarding the ATM transaction after providing the user authentication credential and the data regarding the particular ATM transaction type.

According to some possible implementations, a non-transitory computer-readable medium may store instructions, the instructions may include one or more instructions that, when executed by one or more processors of a user device, cause the one or more processors to receive, from an ATM device, a pairing instruction, the ATM device including a sync button to initiate pairing of the ATM device and the user device, the pairing instruction being based on a user selection of the sync button; communicatively couple to the ATM device based on the pairing instruction; receive, from the ATM device, a request for user authentication credential information after communicatively coupling to the ATM device; cause a first prompt, for a user to input a user authentication credential, to be presented based on receiving the request; detect a user input that includes the user authentication credential after causing the first prompt to be presented; provide, to the ATM device, the user authentication credential based on detecting the user input; obtain, from the ATM device, an authorization to proceed with an ATM transaction after providing the user authentication credential; cause a second prompt, for the user to select an ATM transaction type, to be presented based on obtaining the authorization; detect a user selection of a particular ATM transaction type after causing the second prompt to be presented; and provide, to the ATM device, information regarding the particular ATM transaction type, based on detecting the user selection, to cause the ATM device to perform the ATM transaction.

According to some possible implementations, an ATM device may include a device body, the device body including a sync button to initiate wireless communications with external user devices; a communication interface configured to communicatively couple to external user devices based on user selection of the sync button; one or more memories; and one or more processors communicatively coupled to the one or more memories and the communication interface, the one or more processors being configured to cause the communication interface to provide, to an external user device, a first instruction to prompt a user of the external user device to input personal identification number (PIN) information relating to an account associated with the user; receive, via the communication interface, a PIN provided by the external user device after causing the communication interface to provide the first instruction; perform an action to validate the PIN with respect to the account; cause the communication interface to provide, to the external user device and based on validating the PIN, a second instruction to prompt the user to specify transaction information; and perform an ATM transaction based on the transaction information.

BRIEF DESCRIPTION OF THE DRAWINGS

FIGS. 1A-1I are diagrams of an overview of an example implementation described herein;

FIG. 2 is a diagram of an example environment in which systems and/or methods, described herein, may be implemented;

FIG. 3 is a diagram of example components of one or more devices of FIG. 2;

FIG. 6 is a flow chart of an example process for using an ATM device to interact with a user device to facilitate a transaction.

DETAILED DESCRIPTION

Figure 1A:
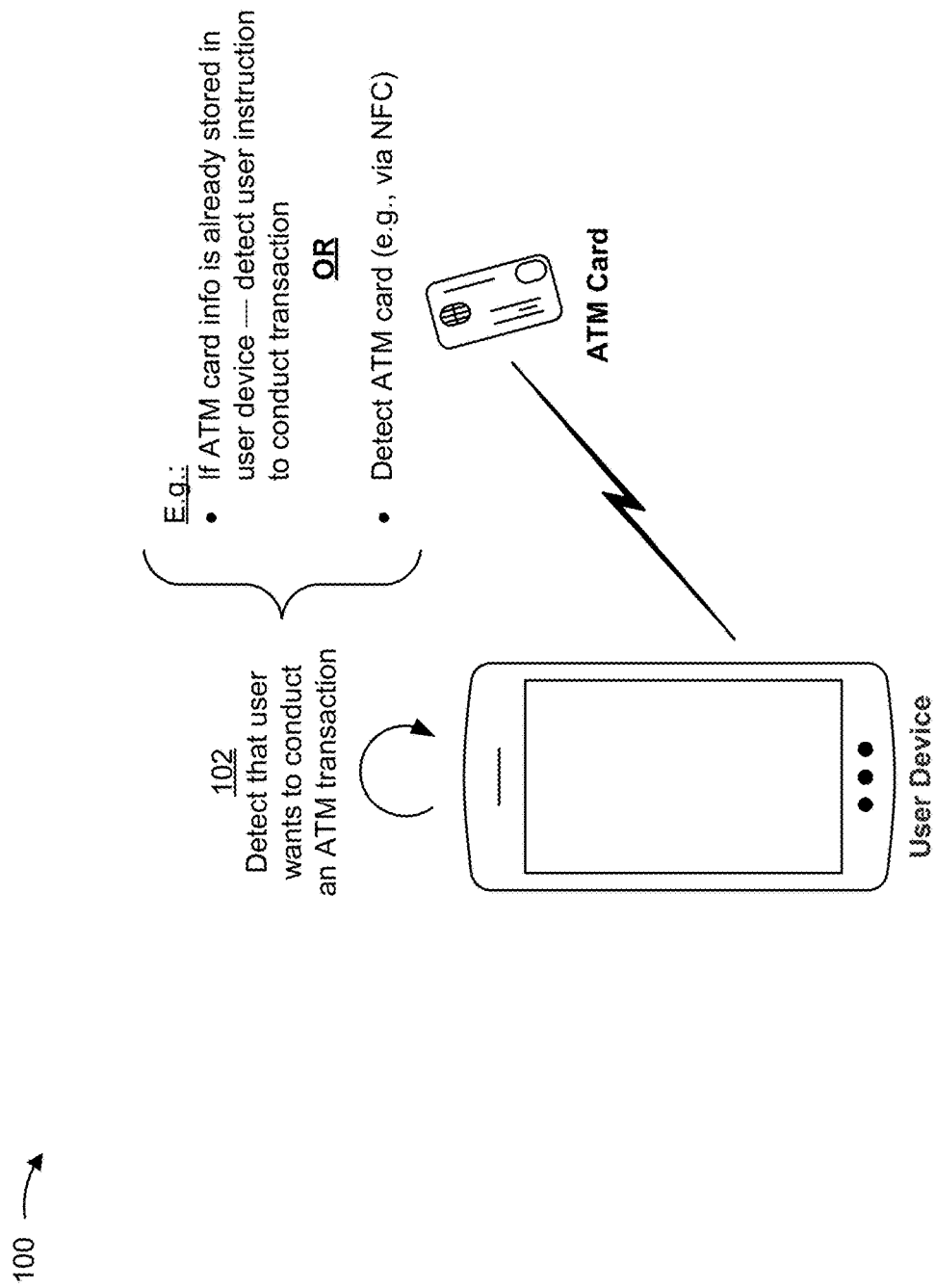

The following detailed description of example implementations refers to the accompanying drawings. The same reference numbers in different drawings may identify the same or similar elements.

In many cases, a user must insert a transaction card into (or swipe a transaction card through) a card reader of an ATM device, and enter a corresponding PIN using a touch screen display or a keypad of the ATM device, in order to conduct an ATM transaction. This introduces the possibility of theft of the user's account data, however, since a malicious user can easily install skimmers, cameras, and/or the like to illicitly capture the user's PIN or transaction card data. Furthermore, user interface components of a typical ATM device, such as a touch screen display and a keypad, are subject to wear and tear, due to frequent use, which increases the costs of maintaining the ATM device.

Some implementations, described herein, provide a user device that is capable of functioning as a user interface for an ATM device. In some implementations, the user device is capable of permitting a user to input the user's authentication credential (e.g., personal identification number (PIN)) and make ATM transaction selection(s), and providing the authentication credential, and information regarding the ATM transaction selection(s), to the ATM device to perform transaction(s). In some implementations, the ATM device lacks user interface components, such as a touch screen display, a keypad, and/or the like, that are typically included in an ATM device. In some implementations, the ATM device may include a user-selectable synchronization ("sync") button that, when selected, enables the ATM device to pair with the user device, and one or more illumination components (e.g., light-emitting diodes (LEDs)) that may be used to provide user notifications.

In this way, an ATM device manufacturer can provide an ATM device that includes fewer components, which simplifies the design and manufacturing of the ATM device, thereby reducing costs. In addition, this reduces or eliminates the possibility of wear and tear of the ATM device that would otherwise occur due to frequent user interaction with user interface components. Furthermore, enabling a user device (e.g., that is external to an ATM device) to function as a user interface of the ATM device reduces or eliminates a need for a user to input the user's PIN directly to the ATM device, which reduces or eliminates the possibility of theft (e.g., via skimmers, cameras, and/or the like) of user account data and improves the overall security of ATM transactions.

FIGS. 1A-1I are diagrams of an overview of an example implementation 100 described herein. Example implementation 100 may include a user device, an ATM card, and an ATM device. The ATM card may include a transaction card, such as a debit card, a credit card, and/or the like. The ATM device may be display-free—that is, the ATM device may not include a display, such as a touch screen display. In some implementations, the ATM device may include no user input components other than a sync button (e.g., described in more detail below).

In some implementations, the user device may include an application—e.g., an ATM transaction application—configured to enable the user device to interact with ATM devices. In some implementations, the application, when executed by one or more processors of the user device, may cause the one or more processors to present a user interface (e.g., various user interface screens) that permits a user to input user authentication credential information, such as a PIN, and make ATM transaction selection(s), prior to proceeding to the ATM device to conduct the transaction(s).

As shown in FIG. 1A, and as shown by reference number 102, the user device may detect that a user wants to conduct an ATM transaction. For example, the user device may detect a presence of the ATM card (e.g., via near-field communication (NFC) and/or the like), and determine that the user wants to conduct an ATM transaction based on detecting the presence of the ATM card. As another example, the user device may detect (e.g., via the user interface) a user input indicating that the user wants to conduct an ATM transaction.

Figure 1B:
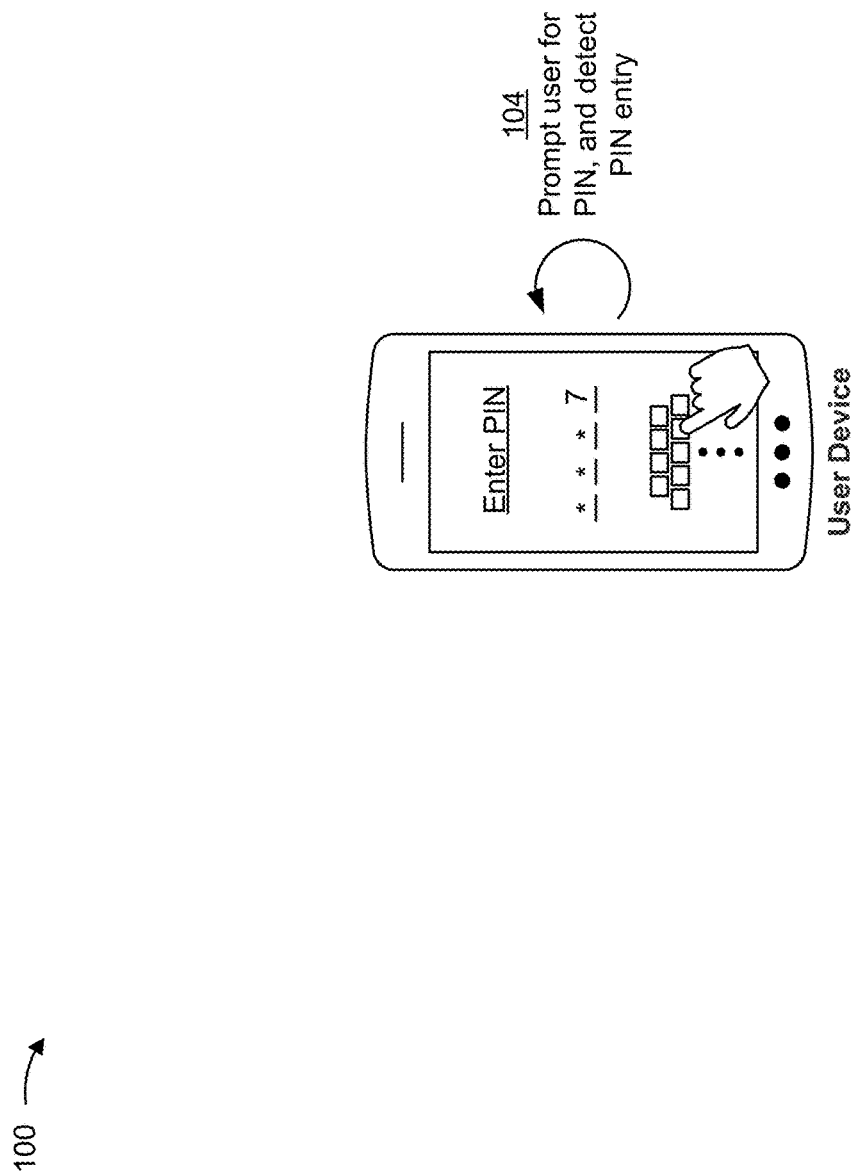

As shown in FIG. 1B, and as shown by reference number 104, the user device may prompt (e.g., via the user interface) the user for a PIN, and detect a PIN entry. As shown in FIG. 1C, and as shown by reference number 106, the user device may store the PIN, and display a user interface screen that prompts the user to select one or more ATM transactions that the user wants to conduct. The ATM transactions may include, for example, a withdrawal of funds from the user's account, a deposit of funds into the user's account, a request for balance information regarding the user's account, and/or the like. As shown by reference number 108, the user may make one or more ATM transaction selection(s).

Figure 1D:
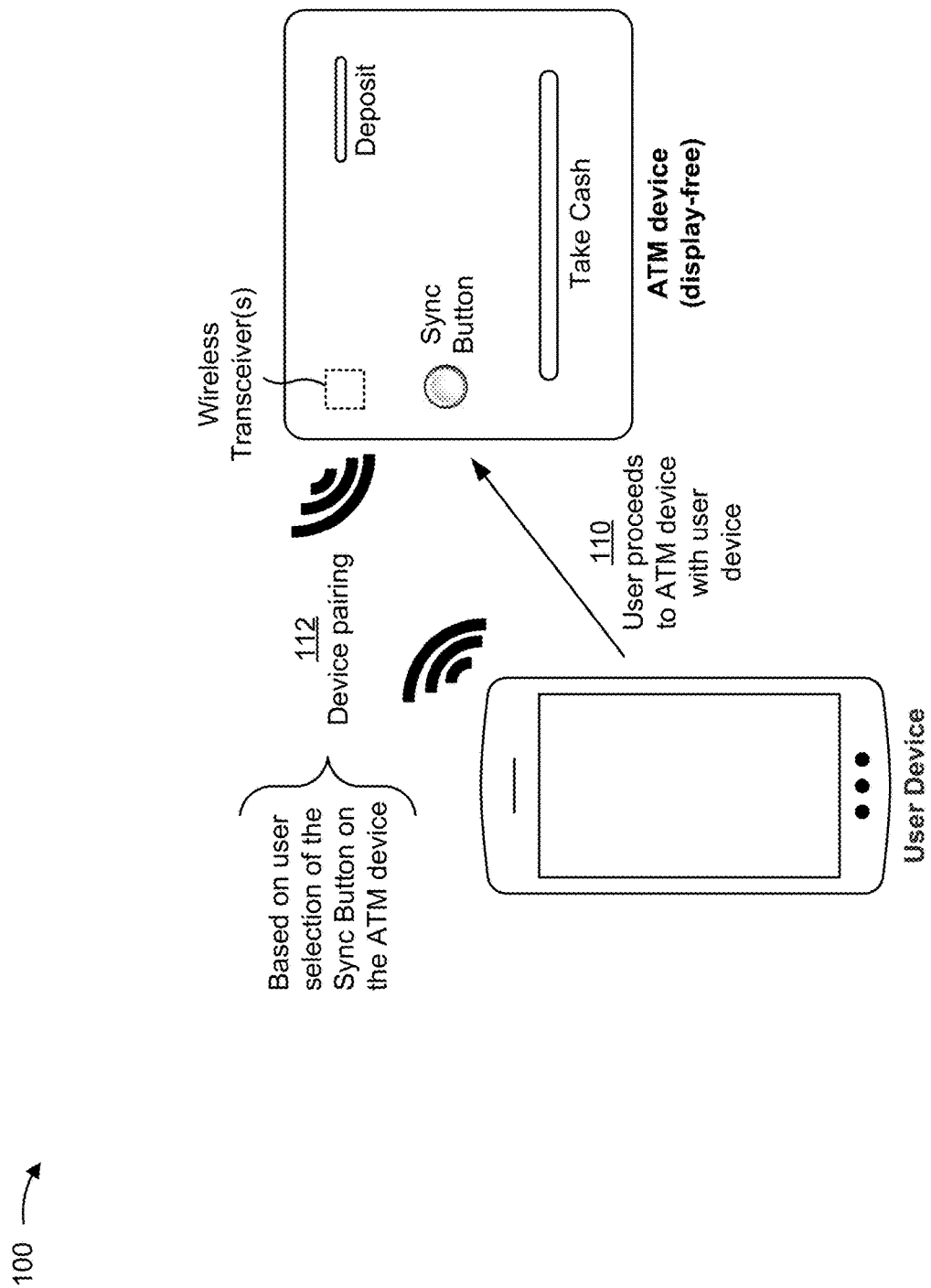

As shown in FIG. 1D, and as shown by reference number 110, the user may proceed to the ATM device with the user device. In some implementations, the user may access the ATM transaction application on the user device when the user is near the ATM device. In some implementations, the ATM transaction application may automatically execute when the user device is near the ATM device. As one example, the user device may automatically cause the ATM transaction application to execute when the user device is located within a threshold distance from the ATM device (e.g., based on a current location of the user device (e.g., as detected by a location-based receiver included in the user device) relative to a known location of the ATM device), when the user device detects one or more signals broadcasted by the ATM device, when the user device receives, from the ATM device, response(s) to signals broadcasted by the user device, and/or the like. As shown by reference number 112, the user device and the ATM device may pair with one another. In some implementations, the ATM device may include a wireless transceiver (e.g., a Bluetooth-based communication interface and/or the like), and a sync button that, when selected by a user, enables the wireless transceiver to initiate wireless communications, such as to communicatively couple with a user device. Here, for example, the user may select the sync button (e.g., by pressing the sync button), and the ATM device may communicatively couple with the user device based on the selection.

In situations where there are multiple ATM devices near one another, and to avoid the possibility of a user device pairing with an unintended ATM device (e.g., an ATM device that is not directly in front of the user of the user device) and a user of the user device mistakenly conducting a transaction with the unintended ATM device, each of the ATM devices may be associated with a unique identifier (e.g., a name or a device ID that includes alphanumeric characters), may be visibly marked (e.g., on a surface of a body of the ATM device in the form of a tag, a plate, an etching (e.g., a laser etching and/or the like), and/or the like) with the unique identifier, and may broadcast a pairing signal (e.g., a Bluetooth-based signal) containing the unique identifier. Here, even if a first user, of a first user device, might select the sync button of a first ATM device, and a second user, of a second user device, might simultaneously (or near simultaneously) select the sync button of a second ATM device, each of the first ATM device and the second ATM device may broadcast the pairing signal, each of the first user device and the second user device may receive such signals and display the corresponding unique identifiers (e.g., as two user-selectable icons) for user selection, and each of the first user and the second user may easily select the appropriate unique identifier based on the visible markings on the first ATM device and the second ATM device.

In some implementations, the ATM device may be configured to terminate a communication session with the user device after the selected transaction(s) are completed. In some implementations, the ATM device may permit a user to end a communication session early by selecting the sync button during the communication session. Additionally, or alternatively, the user device may provide (e.g., via the user interface) a user-selectable input that permits a user to selectively end a communication session early.

In some implementations, the ATM device may include one or more LEDs that can be used to provide one or more status notifications to users. For example, the ATM device may cause an LED to illuminate when the ATM device is successfully paired with a user device. This may, for example, permit a user (e.g., after selecting the sync button and prior to the user's user device providing PIN information to the ATM device for authentication or validation) to ensure, via a visual cue, that the user's user device is paired with an intended ATM device. In addition, this reduces or eliminates the possibility of a user's account information being compromised by thieves, such as via spoofing devices that copy and utilize ATM identifier information to deceive users to sync the users' user devices with the spoofing devices.

In some implementations, the ATM device may cause an LED to illuminate in different manners (e.g., illuminate and remain illuminated for different periods of time, illuminate at different intensities, illuminate in different colors, and/or the like), depending on whether device pairing is successful, whether a correct PIN is inputted, whether the ATM device is out of cash, whether the ATM device is functioning properly, and/or the like. As some examples, the ATM device may cause an LED to illuminate in green when a user's PIN is validated, illuminate in red if an inputted PIN is incorrect, and/or periodically illuminate (e.g., blink) in red if the ATM device is malfunctioning and/or out of cash.

In some implementations, and to thwart attempts by a malicious user to "listen in" and/or record data transmissions between the ATM device and other user devices, the ATM device may employ an encryption protocol (e.g., a hypertext transfer protocol secure (HTTPS)-based protocol and/or the like) to secure the data transmissions.

In some implementations, the ATM device may be configured to prevent a man-in-the-middle (MITM) attack, where a malicious user alters the ATM device's unique identifier to display a unique identifier that is associated with the malicious user's own user device—e.g., a malicious device—such that the malicious device pairs with other user devices attempting to communicatively couple to the ATM device (i.e., in order to function as a pathway between the ATM device and the other user devices), and digitally skims, or steals, data transmitted from the other user devices. To prevent such attacks, the ATM device may be configured to limit a quantity of times that each user device may communicatively couple to the ATM device per unit time (e.g., up to a threshold quantity of connections with the ATM device per day, per hour, and/or the like), limit a duration of each communication session with a user device (e.g., by automatically terminating a communication session upon, or after, completion of a transaction, by automatically terminating a communication session upon, or after, a threshold period of time has elapsed from when the communication session is established, and/or the like). In this way, if a malicious device attempts to communicatively couple to the ATM device after a connection limit has been reached, and/or the like, the ATM device may refuse to further communicatively couple with the malicious device.

In some implementations, the ATM device may be configured to restrict a user device from communicatively coupling to the ATM device for more than a single transaction account. That is, if a malicious device communicatively couples to the ATM device for a first transaction account associated with a first user, and subsequently attempts to communicatively couple to the ATM device for a second transaction account associated with a second user, the ATM device may refuse to communicatively couple with the malicious device. In some implementations, the second user's user device may receive an error (e.g., from the ATM device) when the second user attempts to authenticate (via the malicious device). In some implementations, the error may include information indicating that a different user device needs to be used. Alternatively, the error may not include any additional information so as to obscure a root cause of the error. In some implementations, a user may be permitted to reset, or otherwise disassociate, the user's transaction account from a previously associated user device. In some implementations, the user's user device may be automatically disassociated from the user's transaction account after a predefined period of time, such as after one day, after one week, after one month, and/or the like.

Figure 1E:
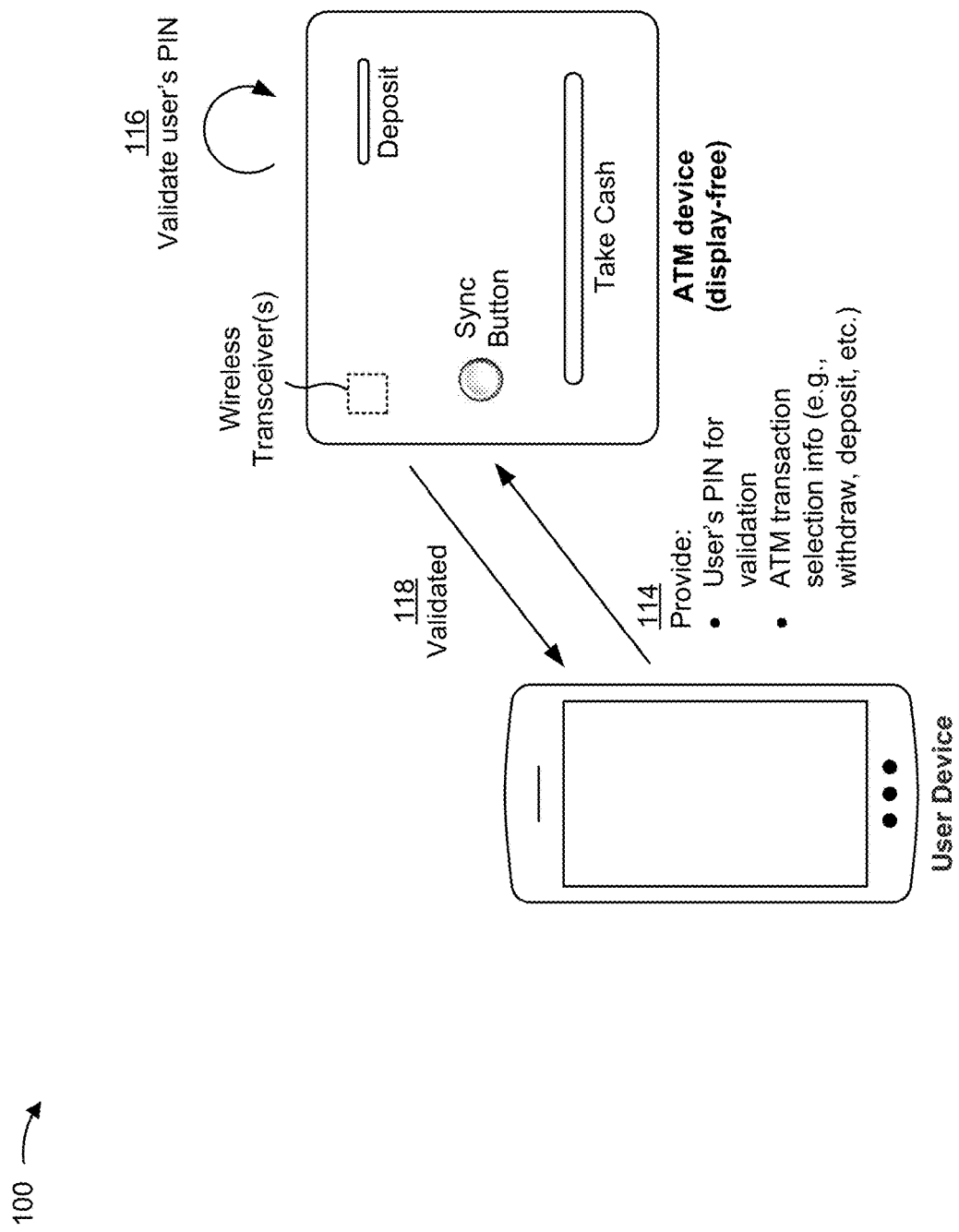

As shown in FIG. 1E, and as shown by reference number 114, the user device may provide, to the ATM device, the user's PIN for validation, and information regarding the ATM transaction selection(s) made by the user (e.g., information regarding whether and how much funds are to be withdrawn, whether and how much funds are to be deposited, whether balance information is to be provided, and/or the like).

As shown by reference number 116, the ATM device may validate the user's PIN. In some implementations, the ATM device may communicate with one or more server devices (e.g., validation device(s)) to validate the PIN. As shown by reference number 118, the ATM device may provide, to the user device, an indication that the user's PIN is validated. In some implementations, the user device may display (e.g., via the user interface) a notification to the user indicating that the user's PIN has been validated.

As shown in FIG. 1F, and as shown by reference number 120, the transaction may then be conducted, depending on user's selected ATM transaction(s). As an example, in a case where the user's selected ATM transaction is to deposit cash, deposit a check, and/or the like, the user device may prompt the user to insert cash and/or check(s) into the ATM device. In some implementations, the indication that the user's PIN is validated (reference number 118) may trigger the user device to prompt the user to insert the cash and/or the check(s). Additionally, or alternatively, and in some implementations, the ATM device may provide, to the user device, a separate instruction to prompt the user to insert the cash and/or the check(s).

As another example, in a case where the user's selected ATM transaction is to withdraw cash, the ATM device may dispense the appropriate amount of cash, and the user device may prompt the user to obtain the cash from the ATM device. In some implementations, the ATM device may provide, to the user device, an instruction to prompt the user to obtain the cash from the ATM device. As yet another example, in a case where the user's selected ATM transaction is to check balance information, the ATM device may provide, to the user device, information regarding a balance of the user's account, which the user device may display to the user.

As described above, the user device may provide a user interface that permits a user to input a PIN and to make ATM transaction selection(s), prior to proceeding to the ATM device to conduct the transaction(s). Alternatively, and in some implementations, the user device and the ATM device may communicatively couple, or pair, with one another, after which the ATM device may cause the user device to present the various user interface screens relating to PIN entry and ATM transaction selection.

Figure 1G:
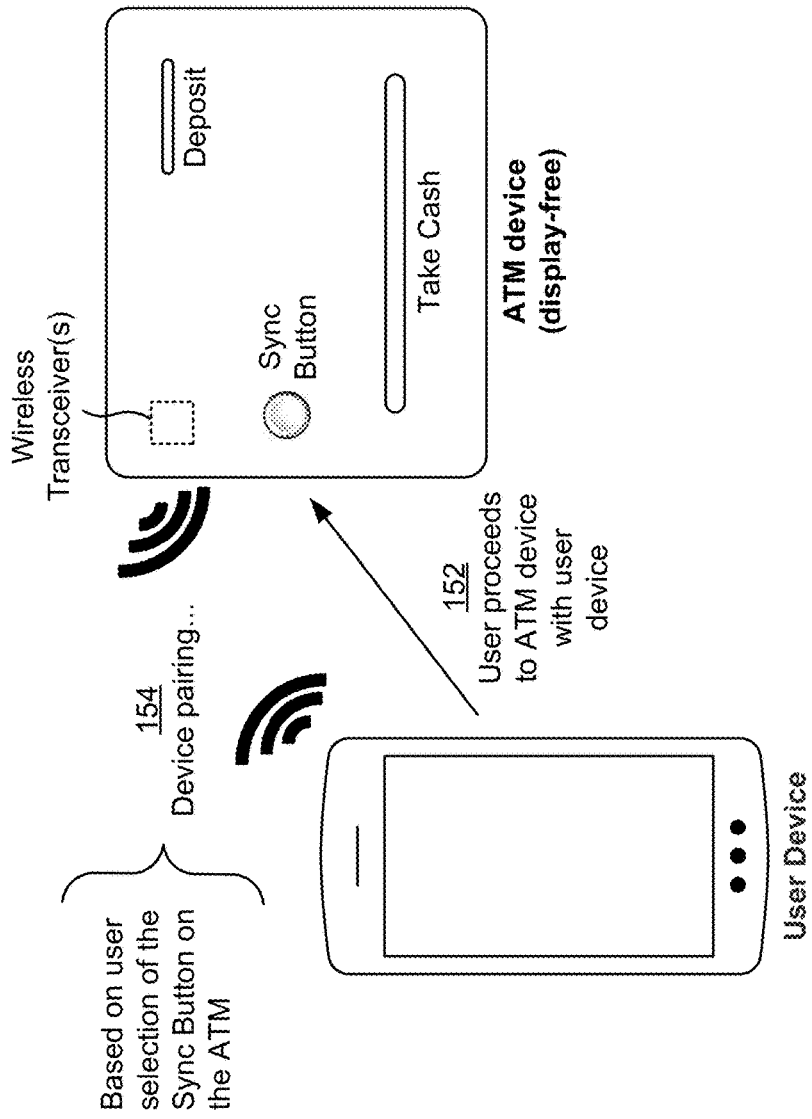

As shown in FIG. 1G, and as shown by reference number 152, the user may proceed to the ATM device with the user device. As shown by reference number 154, the user device and the ATM device may pair with one another. For example, the user may select the sync button of the ATM device, and the user device and the ATM device may pair with one another based on the user's selection, as described above with respect to reference number 112.

Figure 1H:
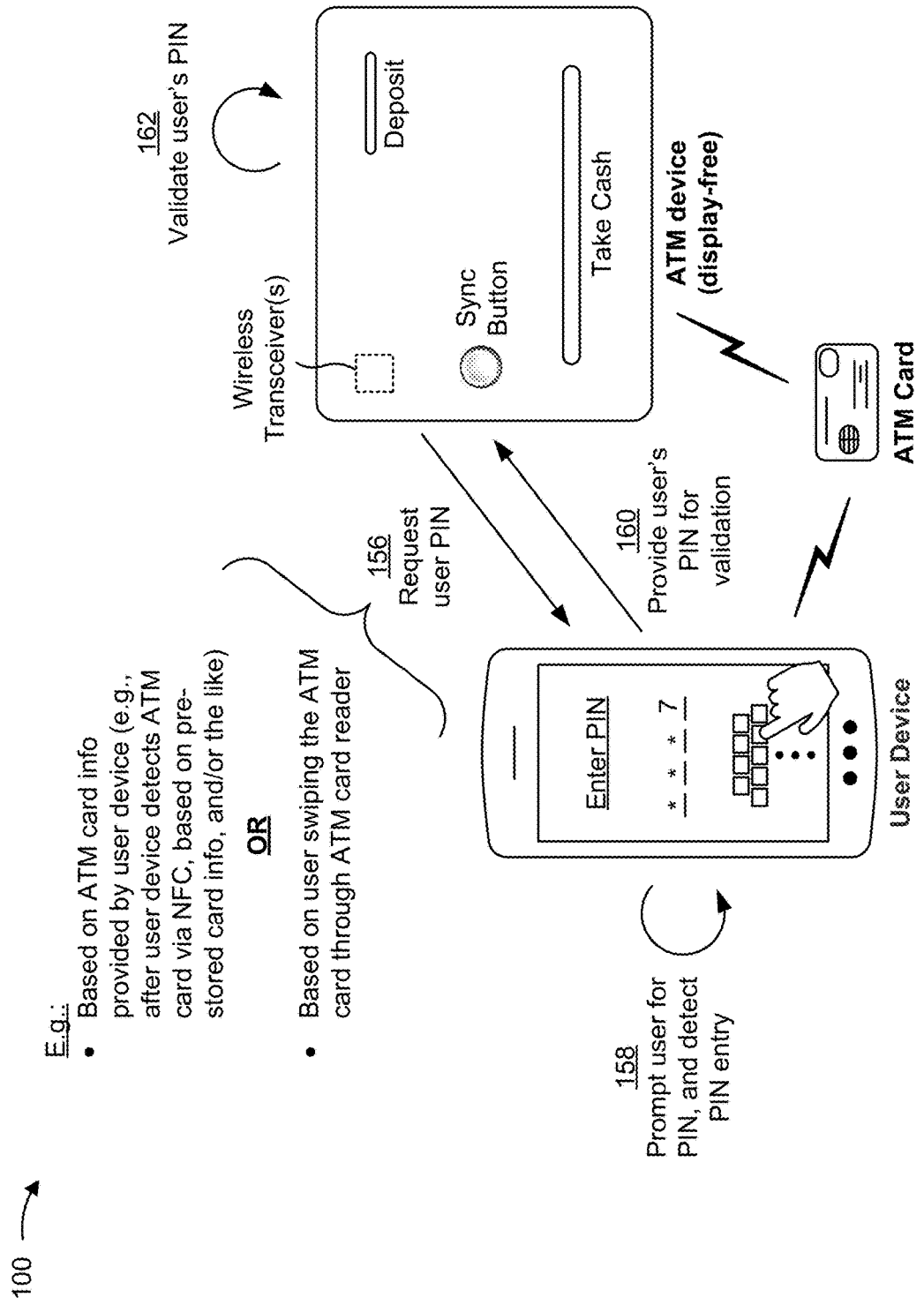

As shown in FIG. 1H, and as shown by reference number 156, the ATM device may instruct the user device to prompt the user for a PIN. In some implementations, the ATM device may include a transaction card reader (e.g., a card insertion or swiping mechanism, a contactless card reading mechanism, and/or the like). In such cases, the ATM device may instruct the user device to prompt the user for a PIN based on the user inserting the ATM card into the transaction card reader, swiping the ATM card through the transaction card reader, and/or tapping the ATM card on (or placing the ATM card near) the transaction card reader. In some implementations, the ATM device may not include a transaction card reader. In such cases, the ATM device may instruct the user device to prompt the user for a PIN based on information, regarding the ATM card, provided by the user device (e.g., after the user device detects the ATM card via NFC, based on card information pre-stored in memory in the user device, and/or the like).

As shown by reference number 158, the user device may display a user interface that prompts the user for a PIN, and detect a PIN entry. As shown by reference number 160, the user device may provide, to the ATM device, the user's PIN for validation. As shown by reference number 162, the ATM device may validate the user's PIN.

Figure 1I:
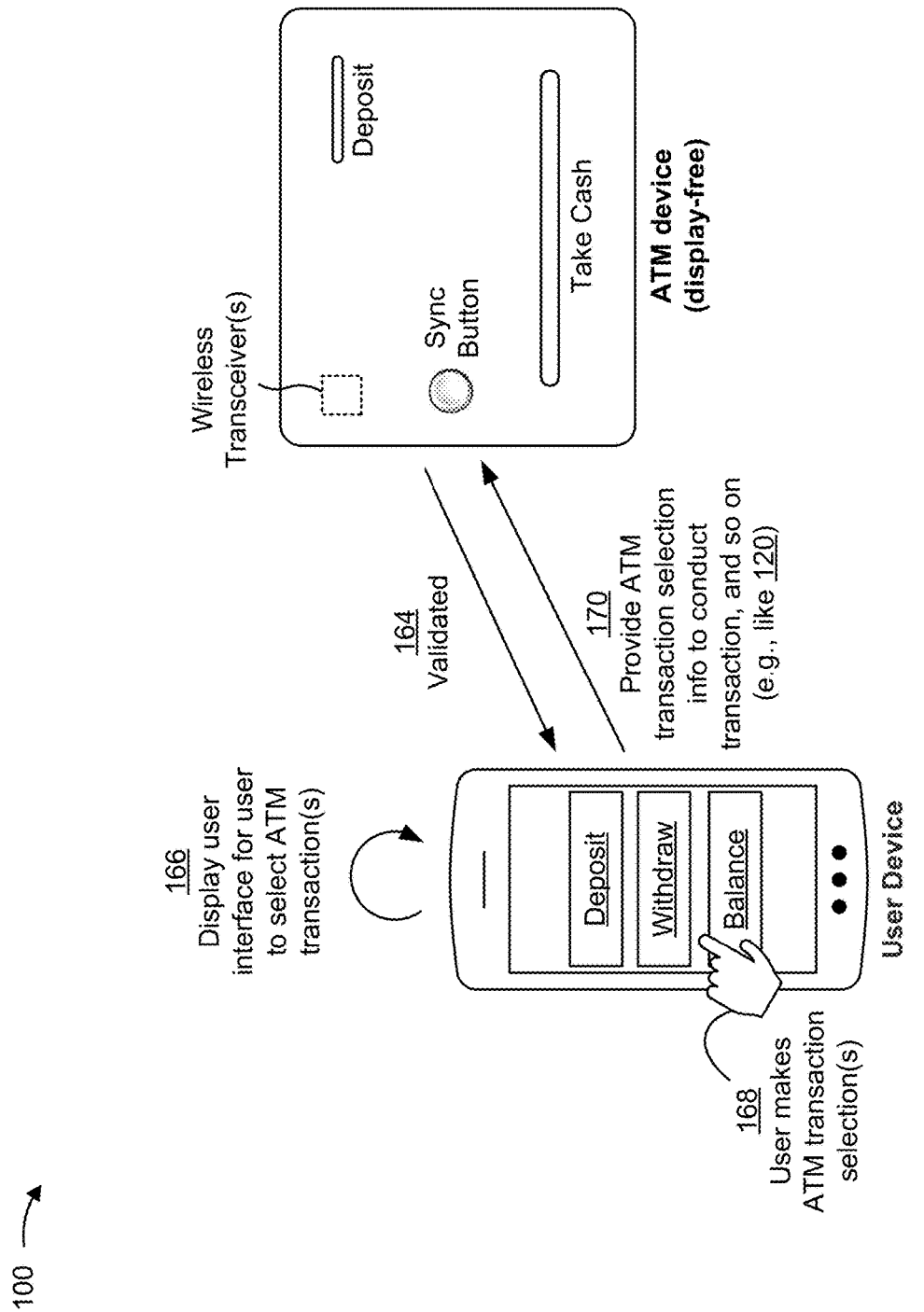

As shown in FIG. 1I, and as shown by reference number 164, the ATM device may provide, to the user device, an indication that the user's PIN is validated. As shown by reference number 166, the user device may display a user interface that prompts the user to select one or more ATM transactions that the user wants to conduct. In some implementations, the indication that the user's PIN is validated (reference number 164) may trigger the user device to prompt the user to select one or more ATM transactions. Additionally, or alternatively, and in some implementations, the ATM device may provide, to the user device, a separate instruction to prompt the user to select one or more ATM transactions.

As shown by reference number 168, the user may make one or more ATM transaction selections via the user interface on the user device. As shown by reference number 170, the user device may provide, to the ATM device, information regarding the ATM transaction selection(s) to cause the ATM device to perform the corresponding transaction(s) (e.g., as described above with respect to reference number 120).

In some implementations, and although not shown, the ATM device may be associated with, and communicatively coupled to (e.g., via a wired connection and/or a wireless connection), a dedicated user device that enables a user to interact with the ATM device to conduct transactions in manners similar to those described above with respect to FIGS. 1A-1I. In some implementations, the dedicated user device may be disposed in proximity to (e.g., disposed within a short distance, such as within several meters and/or the like, from) the ATM device, and may be pre-sync'd with the ATM device. In some implementations, the dedicated user device may be removably attached to a surface (e.g., a wall near the ATM device, a surface of the body of the ATM device, and/or the like), which permits a user, when conducting a transaction at the ATM device, to position and/or orient the dedicated user device according to the user's preference, height, and/or the like.

In this way, an ATM device manufacturer can provide an ATM device that includes fewer components, which simplifies the design and manufacturing of the ATM device, thereby reducing costs. In addition, this reduces or eliminates the possibility of wear and tear of the ATM device that would otherwise occur due to frequent user interaction with user interface components. Furthermore, enabling a user device (e.g., that is external to an ATM device) to function as a user interface of the ATM device reduces or eliminates a need for a user to input the user's PIN directly to the ATM device, which reduces or eliminates the possibility of theft (e.g., via skimmers, cameras, and/or the like) of user account data and improves the overall security of ATM transactions.

As indicated above, FIGS. 1A-1I are provided merely as examples. Other examples are possible and may differ from what was described with regard to FIGS. 1A-1I.

FIG. 2 is a diagram of an example environment 200 in which systems and/or methods, described herein, may be implemented. As shown in FIG. 2, environment 200 may include an ATM device 205 that includes one or more input/output components 210, one or more processors 215, one or more memories 220, and a communication interface 225. Environment 200 may also include one or more validation devices 230, a user device 240, a transaction card 250, and a network 260. Devices of environment 200 may interconnect via wired connections, wireless connections, or a combination of wired and wireless connections.

ATM device 205 includes one or more devices capable of performing various types of financial transactions, such as a cash withdrawal, a money deposit (e.g., a check or cash deposit), a money transfer (e.g., a transfer from one bank account to another bank account), access to information related to an account (e.g., a bank account, a checking account, a credit card account, etc.), and/or the like. For example, ATM device 205 may include an ATM, an automated banking machine (ABM), a cash point, a Cashline®, a Minibank®, a cash machine, a Tyme® machine, a cash dispenser, a Bankomat®, a Bancomat®, and/or a similar type of device.

Input/output component 210 includes one or more devices capable of being used to input information into, and/or output information from, ATM device 205. For example, input/output component 210 may include a user input component (e.g., a sync button, as described elsewhere herein) capable of enabling (e.g., when the user input component is selected by a user) ATM device 205 to communicatively couple to (e.g., pair with) user devices, such as user device 240. As another example, input/output component 210 may include a speaker, an indicator light (e.g., an LED, as described elsewhere herein, and/or the like), a vibrating component, and/or the like that can output information associated with ATM device 205 and/or an action to be performed in connection with an account.

Processor 215 includes one or more types of processing components capable of being programmed to perform a function, such as one or more operations described elsewhere herein. For example, processor 215 may perform process 400 of FIG. 4, process 500 of FIGS. 5A and 5B, process 600 of FIG. 6, and/or the like. In some implementations, processor 215 may correspond to processor 320, described in more detail below in connection with FIG. 3.

Memory 220 includes one or more types of memories capable of storing information. In some implementations, memory 220 may store information associated with performing one or more operations described elsewhere herein. For example, memory 220 may store information to be used (e.g., by processor 215) to perform process 400 of FIG. 4, process 500 of FIGS. 5A and 5B, process 600 of FIG. 6, and/or the like. In some implementations, memory 220 may correspond to memory 330, described in more detail below in connection with FIG. 3.

Communication interface 225 includes one or more types of communication interfaces that allow ATM device 205 to communicate with other devices (e.g., validation device 230, user device 240, transaction card 250, and/or the like), such as via a wired connection, a wireless connection, or a combination of wired and wireless connections. For example, communication interface 225 may be used to read information from transaction card 250, to transmit information to, or receive information from, validation device 230 and/or user device 240, and/or the like. In some implementations, communication interface 225 may correspond to communication interface 370, described in more detail below in connection with FIG. 3.

Validation device 230 includes one or more devices capable of validating user authentication credential information for account access. For example, validation device 230 may include a server, a cloud computing device, a transaction backend, or another type of computing device.

User device 240 includes one or more devices capable of receiving, processing, and/or providing data relating to ATM device 205 and/or transaction card 250. For example, user device 240 may include a smart phone, a tablet computer, a laptop computer, a desktop computer, a wearable device, and/or the like. In some implementations, user device 240 may be capable of functioning as a user interface of ATM device 205, as described elsewhere herein.

Transaction card 250 includes a transaction card that can be used to complete a transaction and/or access account information. For example, transaction card 250 may include a credit card, a debit card, an ATM card, a stored-value card, a fleet card, a transit card, an access card, a virtual card implemented on user device 240, and/or the like. Transaction card 250 may be capable of storing and/or communicating data for a point-of-sale (PoS) transaction and/or an ATM transaction. For example, transaction card 250 may store and/or communicate data, including account information (e.g., an account identifier, a cardholder identifier, etc.), expiration information of transaction card 250 (e.g., information identifying an expiration month and/or year of transaction card 250), banking information (e.g., a routing number of a bank, a bank identifier, etc.), transaction information (e.g., a payment token), and/or the like. For example, to store and/or communicate the data, transaction card 250 may include a magnetic strip and/or an integrated circuit (IC) chip (e.g., a EUROPAY®, MASTERCARD®, or VISA® (EMV) chip). Additionally, or alternatively, transaction card 250 may include an antenna to communicate data associated with transaction card 250. The antenna may be a passive radio frequency (RF) antenna, an active RF antenna, and/or a battery-assisted RF antenna. In some implementations, transaction card 250 may be a smart transaction card, capable of communicating wirelessly (e.g., via Bluetooth, Bluetooth Low Energy (BLE), NFC, and/or the like) with ATM device 205.

Network 260 includes one or more wired and/or wireless networks. For example, network 260 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

FIG. 3 is a diagram of example components of a device 300. Device 300 may correspond to ATM device 205, validation device(s) 230, user device 240, and/or transaction card 250. In some implementations, ATM device 205, validation device(s) 230, user device 240, and/or transaction card 250 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a wireless local area interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
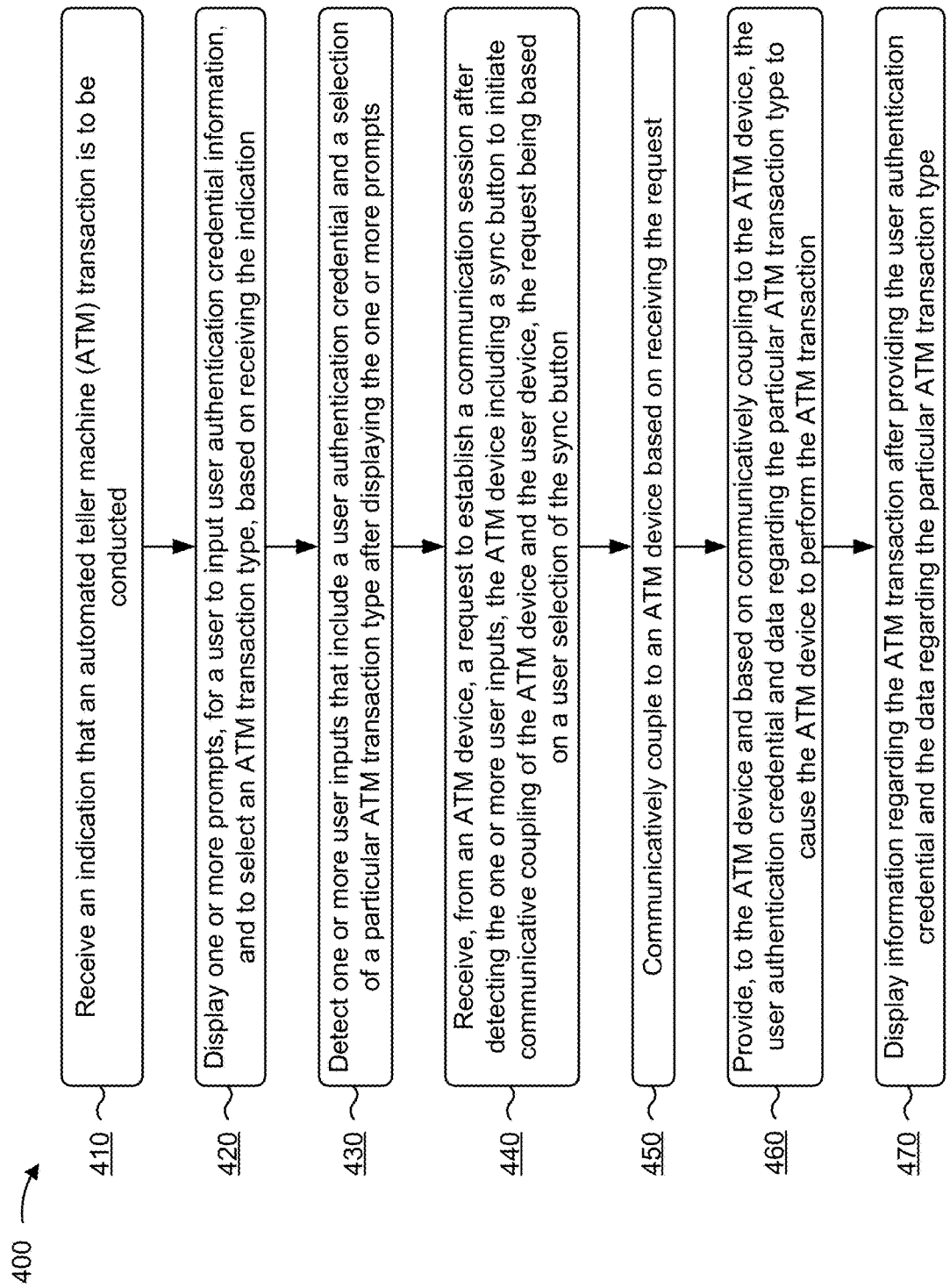
FIG. 4 is a flow chart of an example process for using a user device to interact with an ATM device.

FIG. 4 is a flow chart of an example process 400 for using a user device to interact with an ATM device. In some implementations, one or more process blocks of FIG. 4 may be performed by user device 240. In some implementations, one or more process blocks of FIG. 4 may be performed by another device or a group of devices separate from or including user device 240, such as ATM device 205, validation device 230, and/or transaction card 250.

As shown in FIG. 4, process 400 may include receiving, by a user device (e.g., user device 240), an indication that an ATM transaction is to be conducted (block 410). For example, user device 240 (e.g., using processor 320, memory 330, storage component 340, input component 350, communication interface 370, and/or the like) may receive an indication that an ATM transaction is to be conducted, as described above in connection with FIGS. 1A-1I.

As further shown in FIG. 4, process 400 may include displaying, by the user device, one or more prompts, for a user to input user authentication credential information, and to select an ATM transaction type, based on receiving the indication (block 420). For example, user device 240 (e.g., using processor 320, memory 330, storage component 340, output component 360, communication interface 370, and/or the like) may display one or more prompts, for a user to input user authentication credential information, and to select an ATM transaction type, based on receiving the indication, as described above in connection with FIGS. 1A-1I.

As further shown in FIG. 4, process 400 may include detecting, by the user device, one or more user inputs that include a user authentication credential and a selection of a particular ATM transaction type after displaying the one or more prompts (block 430). For example, user device 240 (e.g., using processor 320, memory 330, storage component 340, input component 350, communication interface 370, and/or the like) may detect one or more user inputs that include a user authentication credential and a selection of a particular ATM transaction type after displaying the one or more prompts, as described above in connection with FIGS. 1A-1I.

As further shown in FIG. 4, process 400 may include receiving, by the user device and from an ATM device (e.g., ATM device 205), a request to establish a communication session after detecting the one or more user inputs, where the ATM device includes a sync button to initiate communicative coupling of the ATM device and the user device, and where the request is based on a selection of the sync button (block 440). For example, user device 240 (e.g., using processor 320, memory 330, storage component 340, communication interface 370, and/or the like) may receive, from ATM device 205, a request to establish a communication session after detecting the one or more user inputs, where ATM device 205 includes a sync button to initiate communicative coupling of ATM device 205 and user device 240, and where the request is based on a user selection of the sync button, as described above in connection with FIGS. 1A-1I.

As further shown in FIG. 4, process 400 may include communicatively coupling, by the user device, to the ATM device based on receiving the request (block 450). For example, user device 240 (e.g., using processor 320, memory 330, storage component 340, communication interface 370, and/or the like) may communicatively couple to ATM device 205 based on receiving the request, as described above in connection with FIGS. 1A-1I.

As further shown in FIG. 4, process 400 may include providing, by the user device, to the ATM device, and based on communicatively coupling to the ATM device, the user authentication credential and data regarding the particular ATM transaction type to cause the ATM device to perform the ATM transaction (block 460). For example, user device 240 (e.g., using processor 320, memory 330, storage component 340, communication interface 370, and/or the like) may provide, to ATM device 205, and based on communicatively coupling to ATM device 205, the user authentication credential and data regarding the particular ATM transaction type to cause ATM device 205 to perform the ATM transaction, as described above in connection with FIGS. 1A-1I.

As further shown in FIG. 4, process 400 may include displaying, by the user device, information regarding the ATM transaction after providing the user authentication credential and the data regarding the particular ATM transaction type (block 470). For example, user device 240 (e.g., using processor 320, memory 330, storage component 340, output component 360, communication interface 370, and/or the like) may display information regarding the ATM transaction after providing the user authentication credential and the data regarding the particular ATM transaction type, as described above in connection with FIGS. 1A-1I.

Process 400 may include additional implementations, such as any single implementation or any combination of implementations described below and/or in connection with one or more other processes described elsewhere herein.

In some implementations, the ATM device may lack user interface components other than the sync button. In some implementations, receiving the indication may include detecting, by the user device, a presence of an ATM transaction card (e.g., transaction card 250), or receiving, by the user device, a user command to conduct the ATM transaction using information associated with the ATM transaction card.

In some implementations, the ATM device may include an illumination component configured to provide user notifications. In some implementations, the user notifications may relate to successful communicatively coupling of the user device and the ATM device, validation of the user authentication credential, an availability of funds in the ATM device, or an operating status of the ATM device.

In some implementations, the user device may initiate a timer after detecting the one or more user inputs, and determine whether the timer has expired prior to providing the user authentication credential and the data regarding the particular ATM transaction type. In some implementations, providing the user authentication credential and the data regarding the particular ATM transaction type may include providing the user authentication credential and the data regarding the particular ATM transaction type further based on determining that the timer has not expired.

In some implementations, the ATM device may include a card reading mechanism. In some implementations, the ATM device may lack user interface components other than the sync button and the card reading mechanism. In some implementations, the user device may receive, from the ATM device, the information regarding the ATM transaction. In some implementations, displaying the information regarding the ATM transaction may include displaying the information regarding the ATM transaction based on receiving the information regarding the ATM transaction.

In some implementations, the information regarding the ATM transaction may include an instruction to the user to insert one or more financial instruments into the ATM device, or to retrieve one or more financial instruments from the ATM device, depending on the particular ATM transaction type.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5A:
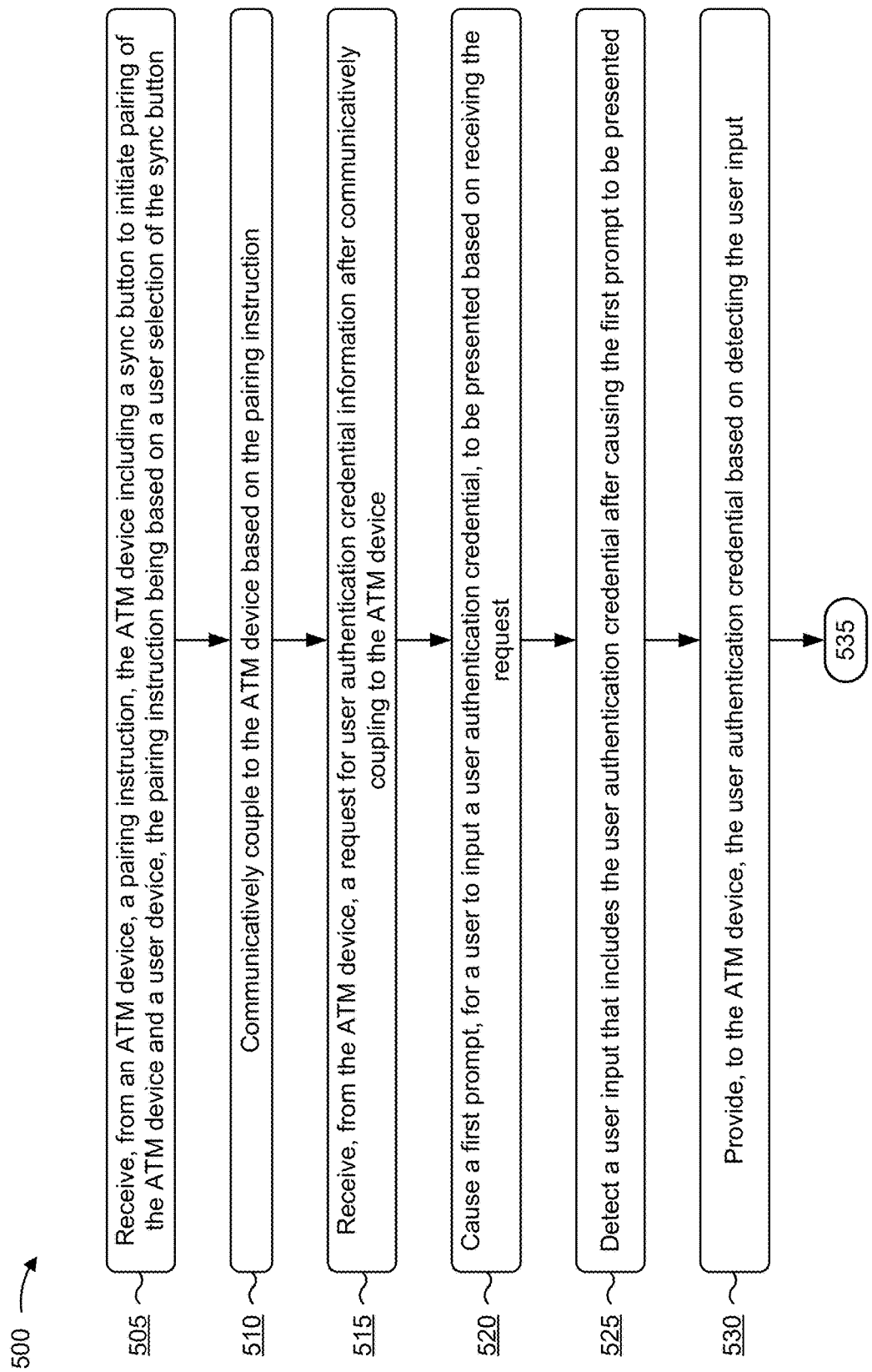
FIGS. 5A and 5B are diagrams of an example process for using a user device to interact with an ATM device.
Figure 5B:
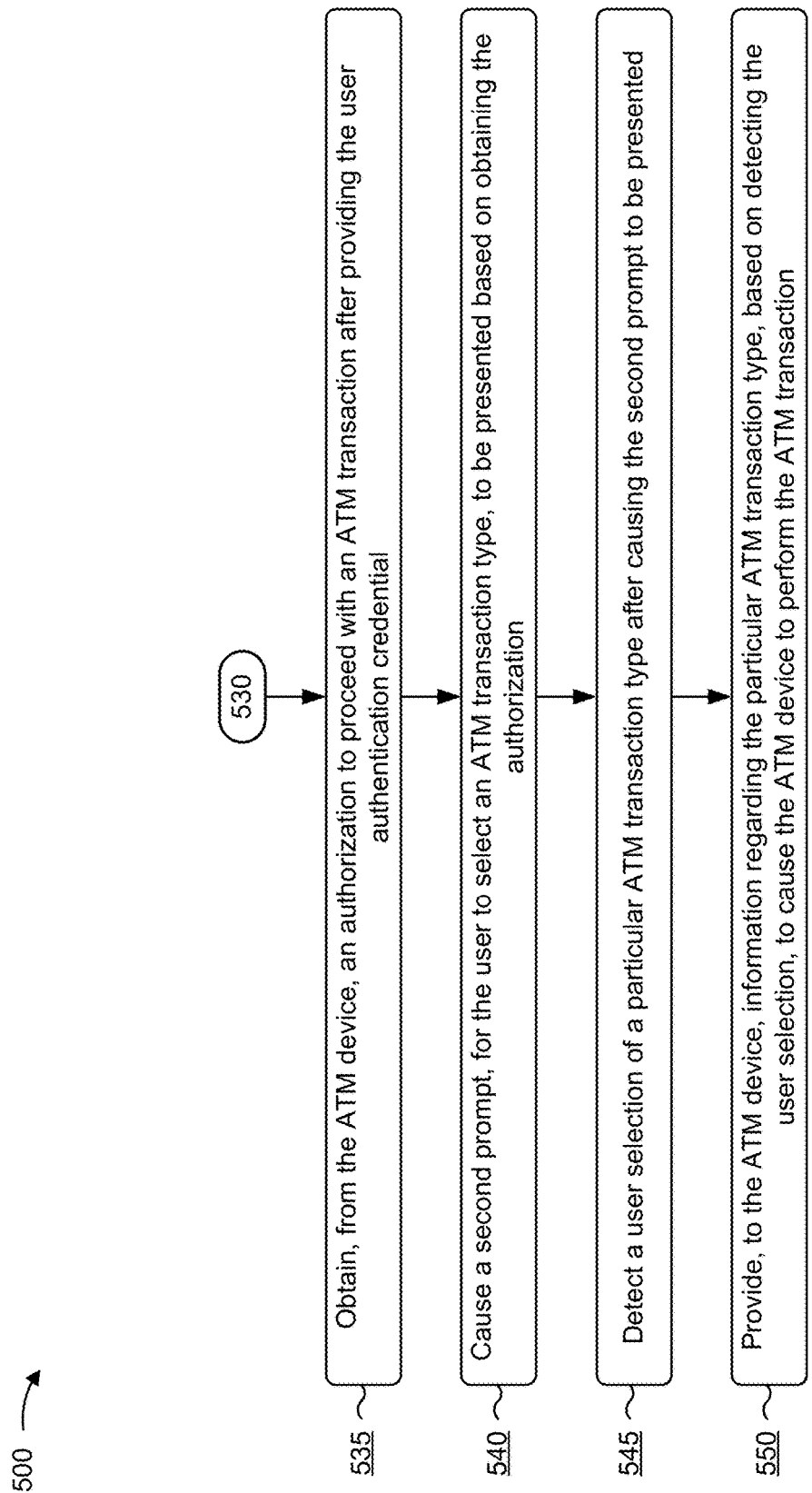

FIGS. 5A and 5B are diagrams of an example process 500 for using a user device to interact with an ATM device. In some implementations, one or more process blocks of FIGS. 5A and 5B may be performed by user device 240. In some implementations, one or more process blocks of FIGS. 5A and 5B may be performed by another device or a group of devices separate from or including user device 240, such as ATM device 205, validation device 230, and/or transaction card 250.

In some implementations, a non-transitory computer-readable medium may store instructions. In some implementations, the instructions may include one or more instructions that, when executed by one or more processors of a user device (e.g., user device 240), cause the one or more processors to perform process 500.

As shown in FIG. 5A, process 500 may include receiving, from an ATM device (e.g., ATM device 205), a pairing instruction, where the ATM device may include a sync button to initiate pairing of the ATM device and the user device, and where the pairing instruction may be based on a user selection of the sync button (block 505). For example, user device 240 (e.g., using processor 320, memory 330, storage component 340, communication interface 370, and/or the like) may receive, from ATM device 205, a pairing instruction, where ATM device 205 may include a sync button to initiate pairing of ATM device 205 and user device 240, and where the pairing instruction may be based on a user selection of the sync button, as described above in connection with FIGS. 1A-1I.

As further shown in FIG. 5A, process 500 may include communicatively coupling to the ATM device based on the pairing instruction (block 510). For example, user device 240 (e.g., using processor 320, memory 330, storage component 340, communication interface 370, and/or the like) may communicatively couple to ATM device 205 based on the pairing instruction, as described above in connection with FIGS. 1A-1I.

As further shown in FIG. 5A, process 500 may include receiving, from the ATM device, a request for user authentication credential information after communicatively coupling to the ATM device (block 515). For example, user device 240 (e.g., using processor 320, memory 330, storage component 340, communication interface 370, and/or the like) may receive, from ATM device 205, a request for user authentication credential information after communicatively coupling to ATM device 205, as described above in connection with FIGS. 1A-1I.

As further shown in FIG. 5A, process 500 may include causing a first prompt, for a user to input a user authentication credential, to be presented based on receiving the request (block 520). For example, user device 240 (e.g., using processor 320, memory 330, storage component 340, output component 360, communication interface 370, and/or the like) may cause a first prompt, for a user to input a user authentication credential, to be presented based on receiving the request, as described above in connection with FIGS. 1A-1I.

As further shown in FIG. 5A, process 500 may include detecting a user input that includes the user authentication credential after causing the first prompt to be presented (block 525). For example, user device 240 (e.g., using processor 320, memory 330, storage component 340, input component 350, communication interface 370, and/or the like) may detect a user input that includes the user authentication credential after causing the first prompt to be presented, as described above in connection with FIGS. 1A-1I.

As further shown in FIG. 5A, process 500 may include providing, to the ATM device, the user authentication credential based on detecting the user input (block 530). For example, user device 240 (e.g., using processor 320, memory 330, storage component 340, communication interface 370, and/or the like) may provide, to ATM device 205, the user authentication credential based on detecting the user input, as described above in connection with FIGS. 1A-1I.

As shown in FIG. 5B, process 500 may include obtaining, from the ATM device, an authorization to proceed with an ATM transaction after providing the user authentication credential (block 535). For example, user device 240 (e.g., using processor 320, memory 330, storage component 340, communication interface 370, and/or the like) may obtain, from ATM device 205, an authorization to proceed with an ATM transaction after providing the user authentication credential, as described above in connection with FIGS. 1A-1I.

As further shown in FIG. 5B, process 500 may include causing a second prompt, for the user to select an ATM transaction type, to be presented based on obtaining the authorization (block 540). For example, user device 240 (e.g., using processor 320, memory 330, storage component 340, output component 360, communication interface 370, and/or the like) may cause a second prompt, for the user to select an ATM transaction type, to be presented based on obtaining the authorization, as described above in connection with FIGS. 1A-1I.

As further shown in FIG. 5B, process 500 may include detecting a user selection of a particular ATM transaction type after causing the second prompt to be presented (block 545). For example, user device 240 (e.g., using processor 320, memory 330, storage component 340, input component 350, communication interface 370, and/or the like) may detect a user selection of a particular ATM transaction type after causing the second prompt to be presented, as described above in connection with FIGS. 1A-1I.

As further shown in FIG. 5B, process 500 may include providing, to the ATM device, information regarding the particular ATM transaction type, based on detecting the user selection of the particular ATM transaction type, to cause the ATM device to perform the ATM transaction (block 550). For example, user device 240 (e.g., using processor 320, memory 330, storage component 340, communication interface 370, and/or the like) may provide, to ATM device 205, information regarding the particular ATM transaction type, based on detecting the user selection of the particular ATM transaction type, to cause ATM device 205 to perform the ATM transaction, as described above in connection with FIGS. 1A-1I.

Process 500 may include additional implementations, such as any single implementation or any combination of implementations described below and/or in connection with one or more other processes described elsewhere herein.

In some implementations, the one or more instructions, when executed by the one or more processors, may further cause the one or more processors to provide, to the ATM device and prior to receiving the request for the user authentication credential information, data relating to a transaction card (e.g., transaction card 250) that is associated with the user.

In some implementations, the one or more instructions, that cause the one or more processors to receive the request, may cause the one or more processors to receive the request based on detection, by the ATM device, of a presence of a transaction card (e.g., transaction card 250) associated with the user.

In some implementations, the particular ATM transaction type may relate to withdrawing financial instruments from the ATM device. In some implementations, the one or more instructions, when executed by the one or more processors, may further cause the one or more processors to receive, from the ATM device, an instruction to prompt the user to obtain a financial instrument from the ATM device.

In some implementations, the particular ATM transaction type may relate to depositing financial instruments into the ATM device. In some implementations, the one or more instructions, when executed by the one or more processors, may further cause the one or more processors to receive, from the ATM device, an instruction to prompt the user to deposit a financial instrument into the ATM device. In some implementations, the ATM device may lack a display screen.

Although FIGS. 5A and 5B show example blocks of process 500, in some implementations, process 500 may include additional blocks, fewer blocks, different blocks, or differently arranged blocks than those depicted in FIGS. 5A and 5B. Additionally, or alternatively, two or more of the blocks of process 500 may be performed in parallel.

FIG. 6 is a flow chart of an example process 600 using an ATM device to interact with a user device to facilitate a transaction. In some implementations, one or more process blocks of FIG. 6 may be performed by ATM device 205. In some implementations, one or more process blocks of FIG. 6 may be performed by another device or a group of devices separate from or including ATM device 205, such as validation device 230, user device 240, and/or transaction card 250.

In some implementations, an ATM device (e.g., ATM device 205) may include a device body. In some implementations, the device body may include a sync button to initiate wireless communications with external user devices (e.g., user devices 240). In some implementations, the ATM device may include a communication interface (e.g., communication interface 225, communication interface 370, and/or the like) configured to communicatively couple to external user devices (e.g., user devices 240) based on a user selection of the sync button, one or more memories (e.g., memory 220, memory 330, and/or the like), and one or more processors (e.g., processor(s) 215, processor 320, and/or the like) communicatively coupled to the one or more memories and the communication interface. In some implementations, the one or more processors may be configured to perform process 600.

As shown in FIG. 6, process 600 may include causing the communication interface to provide, to an external user device, a first instruction to prompt a user of the external user device to input PIN information relating to an account associated with the user (block 610). For example, ATM device 205 (e.g., using processor(s) 215, processor 320, memory 220, memory 330, storage component 340, and/or the like) may cause communication interface 225 and/or communication interface 370 to provide, to an external user device (e.g., user device 240), a first instruction to prompt a user of the external user device to input PIN information relating to an account associated with the user, as described above in connection with FIGS. 1A-1I.

As further shown in FIG. 6, process 600 may include receiving, via the communication interface, a PIN provided by the external user device after causing the communication interface to provide the first instruction (block 620). For example, ATM device 205 (e.g., using processor(s) 215, processor 320, memory 220, memory 330, storage component 340, and/or the like) may receive, via communication interface 225 and/or communication interface 370, a PIN provided by the external user device (e.g., user device 240) after causing communication interface 225 and/or communication interface 370 to provide the first instruction, as described above in connection with FIGS. 1A-1I.

As further shown in FIG. 6, process 600 may include performing an action to validate the PIN with respect to the account (block 630). For example, ATM device 205 (e.g., using processor(s) 215, processor 320, memory 220, memory 330, storage component 340, communication interface 225, communication interface 370, and/or the like) may perform an action to validate the PIN with respect to the account, as described above in connection with FIGS. 1A-1I.

As further shown in FIG. 6, process 600 may include causing the communication interface to provide, to the external user device and based on validating the PIN, a second instruction to prompt the user to specify transaction information (block 640). For example, ATM device 205 (e.g., using processor(s) 215, processor 320, memory 220, memory 330, storage component 340, and/or the like) may cause communication interface 225 and/or communication interface 370 to provide, to the external user device (e.g., user device 240) and based on validating the PIN, a second instruction to prompt the user to specify transaction information, as described above in connection with FIGS. 1A-1I.

As further shown in FIG. 6, process 600 may include performing an ATM transaction based on the transaction information (block 650). For example, ATM device 205 (e.g., using processor(s) 215, processor 320, memory 220, memory 330, storage component 340, and/or the like) may perform an ATM transaction based on the transaction information, as described above in connection with FIGS. 1A-1I.

Process 600 may include additional implementations, such as any single implementation or any combination of implementations described below and/or in connection with one or more other processes described elsewhere herein.

In some implementations, the one or more processors, when causing the communication interface to provide the second instruction, may be configured to cause the communication interface to provide the second instruction to prompt the user to select an ATM transaction type. In some implementations, the one or more processors may be further configured to receive a user selection of the sync button, and cause the communication interface to broadcast a pairing request based on receiving the user selection of the sync button.

In some implementations, the one or more processors may be further configured to receive a pairing response from the external user device after causing the communication interface to broadcast the pairing request, and cause the communication interface to establish a communication session with the external user device based on receiving the pairing response. In some implementations, the device body may lack any user interface components other than the sync button.

In some implementations, the ATM device may further include an additional communication interface configured to detect contactless transaction cards located within a threshold distance from the ATM device. In some implementations, the one or more processors may be further configured to receive, from the additional communication interface, an indication that a contactless transaction card is located within the threshold distance from the ATM device.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Some implementations, described herein, provide a user device 240 that is capable of functioning as a user interface for an ATM device 205. In some implementations, user device 240 is capable of permitting a user to input the user's authentication credential (e.g., personal identification number (PIN)) and make ATM transaction selection(s), and providing the authentication credential, and information regarding the ATM transaction selection(s), to ATM device 205 to perform transaction(s). In some implementations, ATM device 205 lacks user interface components, such as a touch screen display, a keypad, and/or the like, that are typically included in an ATM device. In some implementations, ATM device 205 may include a user-selectable synchronization ("sync") button that, when selected, enables ATM device 205 to pair with user device 240, and one or more illumination components (e.g., light-emitting diodes (LEDs)) that may be used to provide user notifications.

In this way, an ATM device manufacturer can provide an ATM device that includes fewer components, which simplifies the design and manufacturing of the ATM device, thereby reducing costs. In addition, this reduces or eliminates the possibility of wear and tear of the ATM device that would otherwise occur due to frequent user interaction with user interface components. Furthermore, enabling a user device (e.g., that is external to an ATM device) to function as a user interface of the ATM device reduces or eliminates a need for a user to input the user's PIN directly to the ATM device, which reduces or eliminates the possibility of theft (e.g., via skimmers, cameras, and/or the like) of user account data and improves the overall security of ATM transactions.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, and/or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:

1. A method, comprising:
   receiving, by a user device, an indication that an automated teller machine (ATM) transaction is to be conducted,
      wherein the indication is received based on detecting, by the user device, a presence of an ATM transaction card;
   displaying, by the user device, one or more prompts, for a user to input user authentication credential information, and to select an ATM transaction type, based on receiving the indication;
   detecting, by the user device, one or more user inputs that include a user authentication credential and a selection of a particular ATM transaction type after displaying the one or more prompts;
   receiving, by the user device and from an ATM device, a request to establish a communication session after detecting the one or more user inputs,
      the ATM device including a sync button to initiate communicative coupling of the ATM device and the user device, and
      the request being based on a selection of the sync button;
   communicatively coupling, by the user device, to the ATM device based on receiving the request;
   receiving, by the user device, from the ATM device, and via the communication session, data indicating that the ATM transaction card has physically interfaced with the ATM device;
   providing, by the user device, to the ATM device, and based on receiving the data indicating that the ATM transaction card has physically interfaced with the ATM device and based on communicatively coupling to the ATM device, the user authentication credential and data regarding the particular ATM transaction type to cause the ATM device to perform the ATM transaction; and
   displaying, by the user device, information regarding the ATM transaction after providing the user authentication credential and the data regarding the particular ATM transaction type.

2. The method of claim 1, wherein receiving the indication comprises:
   receiving, by the user device, a user command to conduct the ATM transaction using information associated with the ATM transaction card.

3. The method of claim 1, further comprising:
   initiating a timer after detecting the one or more user inputs;
   determining whether the timer has expired prior to providing the user authentication credential and the data regarding the particular ATM transaction type; and
   wherein providing the user authentication credential and the data regarding the particular ATM transaction type comprises:
      providing the user authentication credential and the data regarding the particular ATM transaction type further based on determining that the timer has not expired.

4. The method of claim 1, further comprising:
   receiving, from the ATM device, the information regarding the ATM transaction; and
   wherein displaying the information regarding the ATM transaction comprises:
      displaying the information regarding the ATM transaction based on receiving the information regarding the ATM transaction.

5. The method of claim 1, wherein the information regarding the ATM transaction comprises:
   an instruction to the user to insert one or more financial instruments into the ATM device, or to retrieve one or more financial instruments from the ATM device, depending on the particular ATM transaction type.

6. The method of claim 1, wherein detecting the presence of the ATM transaction card comprises:
   detecting, by the user device, the presence of the ATM transaction card using near-field communication (NFC).

7. The method of claim 1, further comprising:
   automatically executing an application of the user device based on a location of the user device relative to the ATM device,
      the application being used to communicate with the ATM device.

8. A non-transitory computer-readable medium storing instructions, the instructions comprising:
   one or more instructions that, when executed by one or more processors of a user device, cause the one or more processors to:
      receive an indication that an automated teller machine (ATM) transaction is to be conducted,
         wherein the indication is received based on detecting, by the user device, a presence of an ATM transaction card;
      display one or more prompts, for a user to input user authentication credential information, and to select an ATM transaction type, based on receiving the indication;
      detect one or more user inputs that include a user authentication credential and a selection of a particular ATM transaction type after displaying the one or more prompts;
      receive, from an ATM device, a request to establish a communication session after detecting the one or more user inputs,
         the ATM device including a sync button to initiate communicative coupling of the ATM device and the user device, and
         the request being based on a selection of the sync button;
      communicatively couple to the ATM device based on receiving the request;
      receive, from the ATM device, and via the communication session, data indicating that the ATM transaction card has physically interfaced with the ATM device;
      provide, to the ATM device, and based on receiving the data indicating that the ATM transaction card has physically interfaced with the ATM device and based on communicatively coupling to the ATM device, the user authentication credential and data regarding the particular ATM transaction type to cause the ATM device to perform the ATM transaction; and
      display information regarding the ATM transaction after providing the user authentication credential and the data regarding the particular ATM transaction type.

9. The non-transitory computer-readable medium of claim 8, wherein the one or more instructions, when executed by the one or more processors, further cause the one or more processors to:
   provide, to the ATM device, data relating to the ATM transaction card.

10. The non-transitory computer-readable medium of claim 8, wherein the one or more instructions, when executed by the one or more processors, further cause the one or more processors to:
  initiate a timer after detecting the one or more user inputs; and
  determine whether the timer has expired prior to providing the user authentication credential and the data regarding the particular ATM transaction type.

11. The non-transitory computer-readable medium of claim 8, wherein the particular ATM transaction type relates to withdrawing financial instruments from the ATM device; and
  wherein the one or more instructions, when executed by the one or more processors, further cause the one or more processors to:
    receive, from the ATM device, an instruction to prompt the user to obtain a financial instrument from the ATM device.

12. The non-transitory computer-readable medium of claim 8, wherein the particular ATM transaction type relates to depositing financial instruments into the ATM device; and
  wherein the one or more instructions, when executed by the one or more processors, further cause the one or more processors to:
    receive, from the ATM device, an instruction to prompt the user to deposit a financial instrument into the ATM device.

13. The non-transitory computer-readable medium of claim 8, wherein the information regarding the ATM transaction comprises:
  an instruction to the user to insert one or more financial instruments into the ATM device, or to retrieve one or more financial instruments from the ATM device, depending on the particular ATM transaction type.

14. A device, comprising:
  one or more memories; and
  one or more processors, communicatively coupled to the one or more memories, to:
    receive an indication that an automated teller machine (ATM) transaction is to be conducted,
      wherein the indication is received based on detecting, by the device, a presence of an ATM transaction card;
    display one or more prompts, for a user to input user authentication credential information, and to select an ATM transaction type, based on receiving the indication;
    detect one or more user inputs that include a user authentication credential and a selection of a particular ATM transaction type after displaying the one or more prompts;
    receive, from an ATM device, a request to establish a communication session after detecting the one or more user inputs,
      the ATM device including a sync button to initiate communicative coupling of the ATM device and the device, and
      the request being based on a selection of the sync button;
    communicatively couple to the ATM device based on receiving the request;
    receive, by the user device, from the ATM device, and via the communication session, data indicating that the ATM transaction card has physically interfaced with the ATM device;
    provide, to the ATM device, and based on receiving the data indicating that the ATM transaction card has physically interfaced with the ATM device and based on communicatively coupling to the ATM device, the user authentication credential and data regarding the particular ATM transaction type to cause the ATM device to perform the ATM transaction; and
    display information regarding the ATM transaction after providing the user authentication credential and the data regarding the particular ATM transaction type.

15. The device of claim 14, wherein the one or more processors, when receiving the indication, are to:
  receive a user command to conduct the ATM transaction using information associated with the ATM transaction card.

16. The device of claim 14, wherein the one or more processors are further to:
  initiate a timer after detecting the one or more user inputs; and
  determine whether the timer has expired prior to providing the user authentication credential and the data regarding the particular ATM transaction type.

17. The device of claim 14, wherein the one or more processors are further to:
  receive, from the ATM device, the information regarding the ATM transaction; and
  wherein the one or more processors, when displaying the information regarding the ATM transaction, are to:
    display the information regarding the ATM transaction based on receiving the information regarding the ATM transaction.

18. The device of claim 14, wherein the information regarding the ATM transaction comprises:
  an instruction to the user to insert one or more financial instruments into the ATM device, or to retrieve one or more financial instruments from the ATM device, depending on the particular ATM transaction type.

19. The device of claim 14, wherein the particular ATM transaction type relates to withdrawing financial instruments from the ATM device; and
  wherein the one or more processors are further to:
    receive, from the ATM device, an instruction to prompt the user to obtain a financial instrument from the ATM device.

20. The device of claim 14, wherein the particular ATM transaction type relates to depositing financial instruments into the ATM device; and
  wherein the one or more processors are further to:
    receive, from the ATM device, an instruction to prompt the user to deposit a financial instrument into the ATM device.

* * * * *